United States Patent
Dhanak et al.

(10) Patent No.: US 7,091,204 B2
(45) Date of Patent: Aug. 15, 2006

(54) SULFONAMIDES

(75) Inventors: Dashyant Dhanak, King of Prussia, PA (US); Timothy F. Gallagher, Collegeville, PA (US); Steven D. Knight, King of Prussia, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 437 days.

(21) Appl. No.: 10/477,067

(22) PCT Filed: May 7, 2002

(86) PCT No.: PCT/US02/14406

§ 371 (c)(1),
(2), (4) Date: Nov. 7, 2003

(87) PCT Pub. No.: WO02/090348

PCT Pub. Date: Nov. 14, 2002

(65) Prior Publication Data

US 2004/0152891 A1    Aug. 5, 2004

Related U.S. Application Data

(60) Provisional application No. 60/289,327, filed on May 7, 2001.

(51) Int. Cl.
*A61K 31/404* (2006.01)
*A61K 31/495* (2006.01)
*C07D 239/02* (2006.01)
*C07D 207/04* (2006.01)

(52) U.S. Cl. ............... 514/252.1; 548/215; 548/300.1; 548/469; 548/517; 548/527; 548/541; 548/556; 546/268.1; 546/276.4; 544/224; 544/336; 514/256; 514/415; 514/422

(58) Field of Classification Search ............... 548/215, 548/300.1, 469, 517, 527, 541, 556; 546/268.1, 546/276.4; 544/224, 336; 514/252.1, 256, 514/415, 422
See application file for complete search history.

(56) References Cited

U.S. PATENT DOCUMENTS

| 6,423,717 B1 * | 7/2002 | Bromidge et al. ..... 514/252.13 |
| 6,599,904 B1 * | 7/2003 | Bromidge et al. ..... 514/252.13 |
| 6,849,635 B1 * | 2/2005 | Dhanak et al. ............. 514/256 |

FOREIGN PATENT DOCUMENTS

| WO | WO 98/27081 | 6/1998 |
| WO | WO 99/38845 | 11/1999 |

* cited by examiner

*Primary Examiner*—Golam M. M. Shameem
(74) *Attorney, Agent, or Firm*—Linda E. Hall; Stephen A. Venetianer; Charles M. Kinzig

(57) ABSTRACT

The present invention relates to sulfonamides, pharmaceutical compositions containing them, and their use as antagonists of urotensin II.

6 Claims, No Drawings

SULFONAMIDES

This application is a 371 of International Application PCT/US02/14406, filed 7 May 2002; which claims the benefit of U.S. Provisional Application No. 60/289,327, filed 7 May 2001.

FIELD OF THE INVENTION

The present invention relates to sulfonamides, pharmaceutical compositions containing them and their use as urotensin II antagonists

BACKGROUND OF THE INVENTION

The integrated control of cardiovascular homeostasis is achieved through a combination of both direct neuronal control and systemic neurohormonal activation. Although the resultant release of both contractile and relaxant factors is normally under stringent regulation, an aberration in this status quo can result in cardiohemodynamic dysfunction with pathological consequences.

The principal mammalian vasoactive factors that comprise this neurohumoral axis, namely angiotensin-II, endothelin-1, norepinephrine, all function via an interaction with specific G-protein coupled receptors (GPCR). Urotensin-II, represents a novel member of this neurohumoral axis.

In the fish, this peptide has significant hemodynamic and endocrine actions in diverse end-organ systems and tissues:
smooth muscle contraction
    both vascular and non-vascular in origin including smooth muscle preparations from the gastrointestinal tract and genitourinary tract. Both pressor and depressor activity has been described upon systemic administration of exogenous peptide
osmoregulation:
    effects which include the modulation of transepithelial ion ($Na^+$, $Cl^-$) transport. Although a diuretic effect has been described, such an effect is postulated to be secondary to direct renovascular effects (elevated GFR)
metabolism:
    urotensin-II influences prolactin secretion and exhibits a lipolytic effect in fish (activating triacylglycerol lipase resulting in the mobilization of non-esterified free fatty acids)
    (Pearson, et. al. *Proc. Natl. Acad. Sci.* (*U.S.A.*) 1980, 77, 5021; Conlon, et. al. *J. Exp. Zool.* 1996, 275, 226).

In studies with human Urotensin-II it was found that it:
was an extremely potent and efficacious vasoconstrictor
exhibited sustained contractile activity that was extremely resistant to wash out
had detrimental effects on cardiac performance (myocardial contractility)

Human Urotensin-II was assessed for contractile activity in the rat-isolated aorta and was shown to be the most potent contractile agonist identified to date.

Based on the in vitro pharmacology and in vivo hemodynamic profile of human Urotensin-II it plays a pathological role in cardiovascular diseases characterized by excessive or abnormal vasoconstriction and myocardial dysfunction. (Ames et. al. *Nature* 1999, 401, 282; Douglas & Ohlstein (2001). Trends Cardiovasc. Med., 10: in press). Compounds that antagonize the Urotensin-II receptor may be useful in the treatment of congestive heart failure, stroke, ischemic heart disease (angina, myocardial ischemia), cardiac arrhythmia, hypertension (essential and pulmonary), COPD, fibrosis (e.g. pulmonary fibrosis), restenosis, atherosclerosis, dyslipidemia, asthma, (Hay D W P, Luttmann M A, Douglas S A: 2000, *Br J Pharmacol:* 131; 10–12) neurogenic inflammation and metabolic vasculopathies all of which are characterized by abnormal vasoconstriction and/or myocardial dysfunction.

Since U-II and GPR14 are both expressed within the mammalian CNS (Ames et. al. *Nature* 1999, 401, 282), they also may be useful in the treatment of addiction, schizophrenia, cognitive disorders/Alzheimers disease, (Gartlon J. Psychopharmacology (Berl) 2001 June;155(4):426–33), impulsivity, anxiety, stress, depression, pain, migraine, neuromuscular function, parkinsons, movement disorders, sleep-wake cycle, and incentive motivation (Clark et al.*Brain Research* 923 (2001) 120–127.

Functional U-II receptors are expressed in rhabdomyosarcomas cell lines and therefore may have oncological indications. Urotensin may also be implicated in various metabolic diseases such as diabetes (Ames et. al. *Nature* 1999, 401, 282, Nothacker et al., *Nature Cell Biology* 1: 383–385, 1999) and in various gastrointestinal disorders, bone, cartilage, and joint disorders (e.g. arthritis and osteoporosis); and genito-urinary disorders. Therefore, these compounds may be useful for the prevention (treatment) of gastric reflux, gastric motility and ulcers, arthritis, osteoporosis and urinary incontinence.

SUMMARY OF THE INVENTION

In one aspect this invention provides for sulfonamides and pharmaceutical compositions containing them.

In a second aspect, this invention provides for the use of sulfonamides as antagonists of urotensin II, and as inhibitors of urotensin II.

In another aspect, this invention provides for the use of sulfonamides for treating conditions associated with urotensin II imbalance.

In yet another aspect, this invention provides for the use of sulfonamides for the treatment of congestive heart failure, stroke, ischemic heart disease (angina, myocardial ischemia), cardiac arrhythmia, hypertension (essential and pulmonary), renal disease (acute and chronic renal failure/end stage renal disease) along with peripheral vascular disease (male erectile dysfunction, diabetic retinopathy, intermittent claudication/ischemic limb disease) and ischemic/hemorrhagic stroke, COPD, restenosis, asthma, neurogenic inflammation, migraine, metabolic vasculopathies, bone/cartilage/joint diseases, arthritis and other inflammatory diseases, fibrosis (e.g. pulmonary fibrosis), sepsis, atherosclerosis, dyslipidemia, addiction, schizophrenia, cognitive disorders/Alzheimers disease, impulsivity, anxiety, stress, depression, parkinsons, movement disorders, sleep-wake cycle, incentive motivation, pain, neuromuscular function, diabetes, gastric reflux, gastric motility disorders, ulcers and genitourinary diseases.

The urotensin antagonist may be administered alone or in conjunction with one or more other therapeutic agents, said agents being selected from the group consisting of endothelin receptor antagonists, angiotensin converting enzyme (ACE) inhibitors, A-II receptor antagonists, vasopeptidase inhibitors, diuretics, digoxin, and dual non-selective $\beta$-adrenoceptor and $\alpha_1$-adrenoceptor antagonists.

Other aspects and advantages of the present invention are described further in the following detailed description of the preferred embodiments thereof.

DETAILED DESCRIPTION OF THE INVENTION

The present invention provides for compounds of Formula (I):

The present invention provides for compounds of Formula (I):

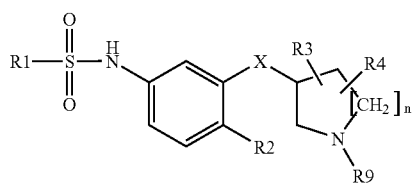

Formula (I)

wherein:
$R_1$ is phenyl, thienyl, furanyl, pyrroyl, pyridinyl, oxazoyl, indoyl, triazinyl, imidazoyl, pyrimidinyl, oxadiazoyl, pyrazoyl, triazoyl, thiazoyl, thiadiazoyl, or pyrazinyl substituted or unsubstituted by one, two, three, four or five of any of the following: halogen, $CF_3$, $OCF_3$, $SCF_3$, $NO_2$, CN, $C_{1-6}$ alkyl, $C_{1-6}$ alkoxy, $NR_5R_6$, $CONR_7R_8$, $SC_{1-6}$ alkyl, $CO_2(C_{1-6}$ alkyl), or $C_{1-6}$ alkyl-$CO_2(C_{1-6}$ alkyl);
$R_2$ is hydrogen, halogen, $CF_3$, CN, or $C_{1-4}$ alkyl;
$R_3$, $R_4$, $R_7$, and $R_8$ are independently hydrogen, $C_{1-6}$ alkyl, or benzyl;
$R_5$, $R_6$, and $R_9$, are independently hydrogen or $C_{1-6}$ alkyl;
X is O, S, or $CH_2$;
n is 0, 1, or 2;
or a pharmaceutically acceptable salt thereof;
provided when n is 1, $R_1$ is not phenyl.

When used herein, the term "alkyl" includes all straight chain and branched isomers. Representative examples thereof include methyl, ethyl, n-propyl, iso-propyl, n-butyl, sec-butyl, iso-butyl, t-butyl, n-pentyl and n-hexyl.

When used herein, the terms 'halogen' and 'halo' include fluorine, chlorine, bromine and iodine and fluoro, chloro, bromo and iodo, respectively.

The compounds of the present invention may contain one or more asymmetric carbon atoms and may exist in racemic and optically active form. All of these compounds and their diastereoisomers are contemplated to be within the scope of the present invention.

Preferably $R_1$ is phenyl, thienyl, or furanyl substituted or unsubstituted by one, two, three, four, or five of any of the following: halogen, $CF_3$, $OCF_3$, CN, $C_{1-6}$ alkyl, $C_{1-6}$ alkoxy, $CO_2(C_{1-6}$ alkyl), $C_{1-6}$ alkyl-$CO_2(C_{1-6}$ alkyl), or $NO_2$.
Preferably $R_2$ is hydrogen, halogen, $CF_3$, or $C_{1-4}$ alkyl; more preferrably halogen or $CF_3$.
Preferably $R_3$ is hydrogen.
Preferably $R_4$ is hydrogen.
Preferably $R_9$ is hydrogen or $C_{1-6}$ alkyl.
Preferably X is O.
Preferably n is 1.
Preferred compounds are:
(S)-N-[4-Chloro-3-(1-methyl-3-pyrrolidinyloxy)-phenyl]-4,5-dibromothiophene-2-sulfonamide;
(R)-N-[4-Chloro-3-(1-methyl-3-pyrrolidinyloxy)-phenyl]-4,5-dibromothiophene-2-sulfonamide;
(R)-N-[4-Chloro-3-(1-methyl-3-pyrrolidinyloxy)-phenyl]-4-bromo-5-chlorothiophene-2-sulfonamide;
(R)-N-[4-Chloro-3-(1-methyl-3-pyrrolidinyloxy)-phenyl]-4-bromo-2,5-dichlorothiophene-3-sulfonamide;
(R)-N-[4-Chloro-3-(1-methyl-3-pyrrolidinyloxy)-phenyl]-2,4,5-trichloro-thiophene-3-sulfonamide;
(R)-N-[4-Chloro-3-(1-methyl-3-pyrrolidinyloxy)-phenyl]-2,5-dichloro-4-methyl-thiophene-3-sulfonamide;
4-Bromo-2,5-dichloro-thiophene-3-sulfonic acid [4-methyl-3-((R)-1-methyl-pyrrolidin-3-yloxy)-phenyl]-amide;
4-Bromo-2,5-dichloro-thiophene-3-sulfonic acid [4-methyl-3-((S)-1-methyl-pyrrolidin-3-yloxy)-phenyl]-amide;
4-Bromo-2,5-dichlorohiophene-3-sulfonic acid [3-(1-methyl-pyrrolidin-3-yloxy)-4-trifluoromethyl-phenyl]-amide;
4-Bromo-5-chloro-thiophene-2-sulfonic acid [3-((R)-1-methyl-pyrrolidin-3-yloxy)-4-trifluoromethyl-phenyl]-amide;
4,5-Dibromo-thiophene-2-sulfonic acid [3-((R)-1-methyl-pyrrolidin-3-yloxy)-4-trifluoromethyl-phenyl]-amide;
2,5-Dichloro-thiophene-3-sulfonic acid [3-((R)-1-methyl-pyrrolidin-3-yloxy)-4-trifluoromethyl-phenyl]-amide;
5-Bromo-6-chloro-pyridine-3-sulfonic acid [3-((R)-1-methyl-pyrrolidin-3-yloxy)-4-trifluoromethyl-phenyl]-amide;
2,4,5-Trichloro-thiophene-3-sulfonic acid [3-((R)-1-methyl-pyrrolidin-3-yloxy)-4-trifluoromethyl-phenyl]-amide;
(R)-N-[4-Chloro-3-(1-methyl-3-pyrrolidinyloxy)-phenyl]-(2,5-dimethyl-4-ethoxycarbonyl)-furan-3-sulfonamide;
2,4-Dimethoxy-pyrimidine-5-sulfonic acid [4-chloro-3-((R)-1-methyl-pyrrolidin-3-yloxy)-phenyl]-amide;
2,4-Diethoxy-pyrimidine-5-sulfonic acid [4-chloro-3-((R)-1-methyl-pyrrolidin-3-yloxy)-phenyl]-amide;
2-Chloro-4-(2,2,2-trifluoro-ethoxy)-pyrimidine-5-sulfonic acid [4-chloro-3-((R)-1-methyl-pyrrolidin-3-yloxy)-phenyl]-amide;
5-Bromo-6-chloro-pyridine-3-sulfonic acid [4-chloro-3-((R)-1-methyl-pyrrolidin-3-yloxy)-phenyl]-amide; or
5-Bromo-6-chloro-pyridine-3-sulfonic acid [4-methyl-3-((R)-1-methyl-pyrrolidin-3-yloxy)-phenyl]-amide.

More preferred compounds are:
(R)-N-[4-Chloro-3-(1-methyl-3-pyrrolidinyloxy)-phenyl]-4-bromo-2,5-dichlorothiophene-3-sulfonamide;
4-Bromo-2,5-dichloro-thiophene-3-sulfonic acid N-[3-(1-methyl-pyrrolidin-3-yloxy)-4-trifluoromethyl-phenyl]-amide; or
2,4,5-Trichloro-thiophene-3-sulfonic acid [3-((R)-1-methyl-pyrrolidin-3-yloxy)-4-trifluoromethyl-phenyl]-amide.

Compounds of Formula (I) may be prepared as outlined in Scheme 1.

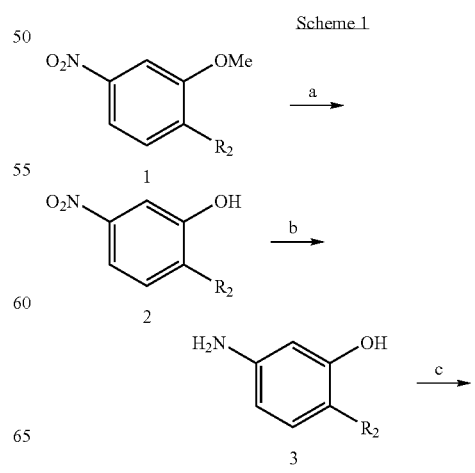

Scheme 1

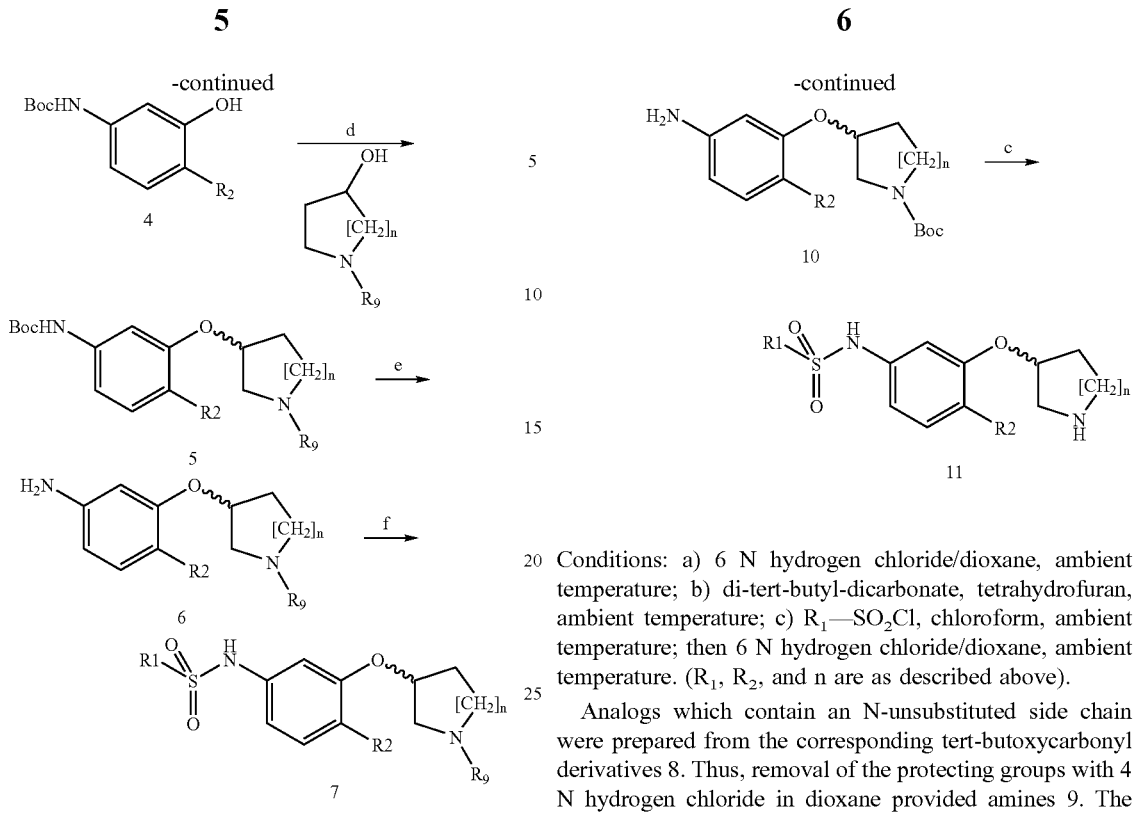

Conditions: a) 48% hydrogen bromide, acetic acid; b) hydrogen (50 psi), platinum on carbon, ethyl acetate; c) di-tert-butyldicarbonate, tetrahydrofuran, reflux; d) DIAD, triphenylphosphine, tetrahydrofuran, 0° C. to ambient temperature; e) 6 N HCl in dioxane; f) $R_1SO_2Cl$, chloroform, ambient temperature. ($R_1$, $R_2$, $R_9$, and n are as described above)

For example, acid-mediated demethylation of anisoles 1 gave phenols 2. Hydrogenation of the nitro group provided anilines 3, which were subsequently protected as their tert-butoxycarbonyl carbamates 4. Alkylation of 4 with various alcohols using standard Mitsunobu conditions, followed by removal of the nitrogen protecting group afforded anilines 6. Subsequent sulfonylation of the anilines furnished the target compounds 7.

Analogs which contain an N-unsubstituted side chain may be prepared according to scheme 2.

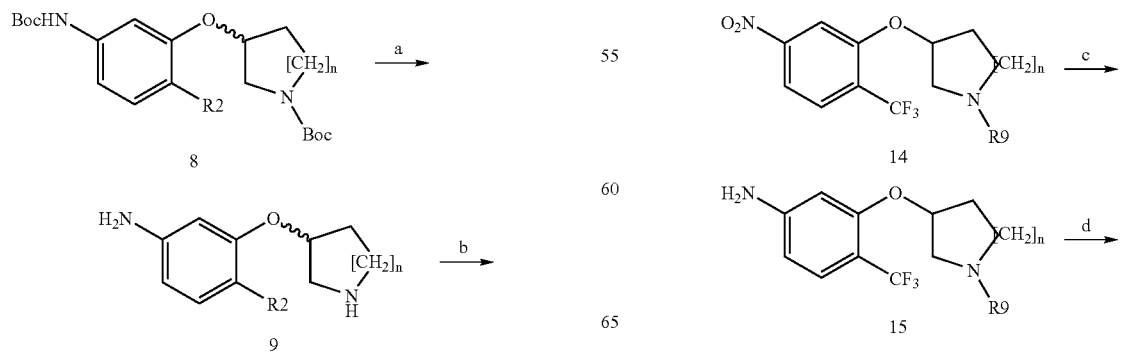

Conditions: a) 6 N hydrogen chloride/dioxane, ambient temperature; b) di-tert-butyl-dicarbonate, tetrahydrofuran, ambient temperature; c) $R_1$—$SO_2Cl$, chloroform, ambient temperature; then 6 N hydrogen chloride/dioxane, ambient temperature. ($R_1$, $R_2$, and n are as described above).

Analogs which contain an N-unsubstituted side chain were prepared from the corresponding tert-butoxycarbonyl derivatives 8. Thus, removal of the protecting groups with 4 N hydrogen chloride in dioxane provided amines 9. The secondary amine was selectively protected as its tert-butyl carbamate to furnish 10. Sulfonylation of 10, followed by protecting group removal afforded the target compounds 11.

Compounds wherein $R_2$ is $CF_3$ may be prepared as follows:

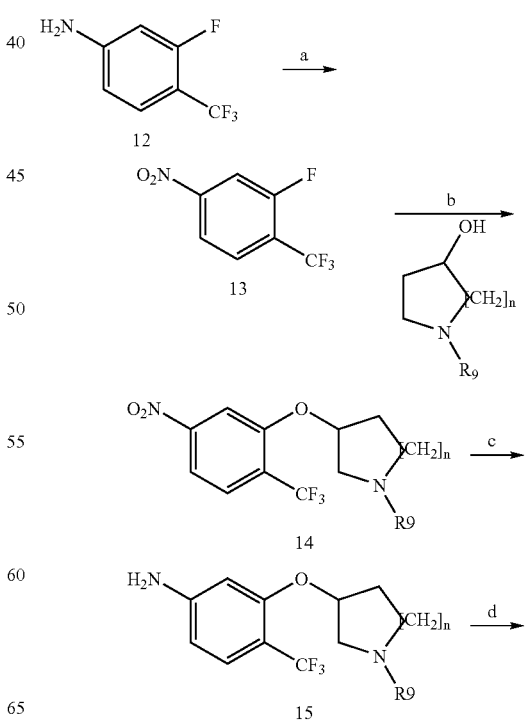

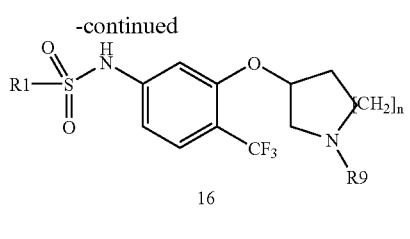

Conditions: a) 50% hydrogen peroxide, trifluoroacetic acetic acid, reflux; b) 1-R9-pyrrolidin-3-ol, sodium hydride, tetrahydrofuran, 0° C.; c) hydrogen (50 psi), platinum on carbon, ethyl acetate; d) $R_1$—$SO_2Cl$, chloroform, room temperature. ($R_1$, $R_9$, and n are as described above)

For example, oxidation of aniline 12 gave nitrobenzene 13. Substitution of the aryl fluoride with various alcohols furnished the ethers 14. Hydrogenation of the nitro group provided anilines 15, which were subsequently sulfonylated with variuos sulfonyl chlorides to furnish the target compounds 16.

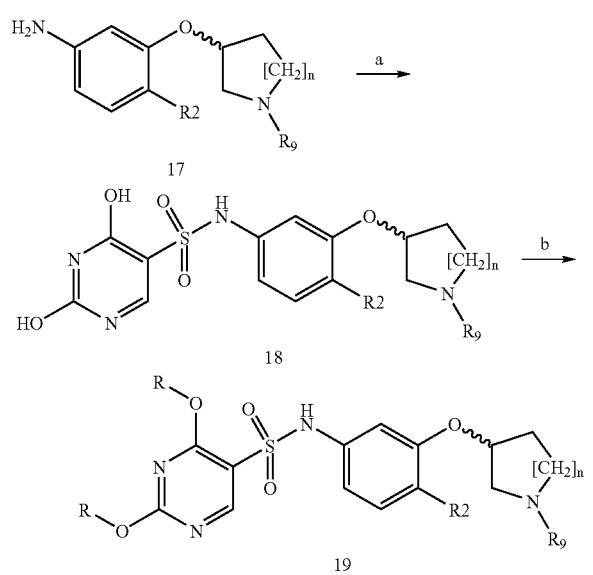

Conditions: a) 2,4-Dihydroxy-pyrimidine-5-sulfonyl chloride, pyridine, ambient temperature; b) phosphorus(III)oxychloride, reflux; then R—OH, ambient temperature. (R is $C_{1-6}$ alkyl, $R_2$, $R_9$, and n are as described above).

For example, aniline 17 was sulfonylated with 2,4-dihydroxy-pyrimidine-5-sulfonyl chloride to give sulfonamide 18. Treatment of 18 with various alcohols furnished the desired compounds 19.

With appropriate manipulation, including the use of alternative nitrogen protecting group(s), the synthesis of the remaining compounds of Formula (I) was accomplished by methods analogous to those above and to those described in the Experimental section.

A number of optionally substituted benzenesulfonyl chlorides used in the synthesis of the title compounds were not available commercially and were prepared according to schemes 5, 6, and 7. 2,4-Dibromo-5-methoxybenzenesulfonyl chloride was prepared as described in WO9838182 and 2,4-dihydroxypyrimidine-5-sulfonyl chloride was prepared as described in J. Am. Chem. Soc. 1956, 78, 401.

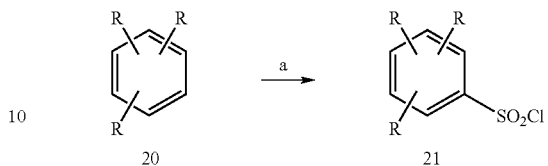

Substituted benzenes 20 were treated with chlorosulfonic acid to furnish the desired sulfonyl chlorides 21. (R is as defined for $R_1$).

Conditions: a) chlorosulfonic acid, dichloromethane, 0° C. to ambient temperature.

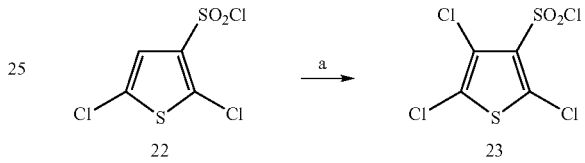

Conditions: a) sulfur monochloride, aluminum trichloride, sulfuryl chloride, 60° C.

Chlorination of thiophene 22 furnished the desired sulfonyl chloride 23.

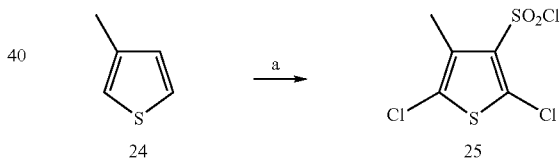

Conditions: a) sulfuryl chloride, dichloromethane, ambient temperature; then chlorosulfonic acid.

Thiophene 24 was treated with chlorosulfonic acid to furnish the desired sulfonyl chloride 25.

In order to use a compound of the Formula (I) or a pharmaceutically acceptable salt thereof for the treatment of humans and other mammals it is normally formulated in accordance with standard pharmaceutical practice as a pharmaceutical composition.

Compounds of Formula (I) and their pharmaceutically acceptable salts may be administered in a standard manner for the treatment of the indicated diseases, for example orally, parenterally, sub-lingually, transdermally, rectally, via inhalation or via buccal administration.

Compounds of Formula (I) and their pharmaceutically acceptable salts which are active when given orally can be formulated as syrups, tablets, capsules and lozenges. A syrup formulation will generally consist of a suspension or solution of the compound or salt in a liquid carrier for example, ethanol, peanut oil, olive oil, glycerine or water with a flavoring or coloring agent. Where the composition is in the form of a tablet, any pharmaceutical carrier routinely used for preparing solid formulations may be used. Examples of such carriers include magnesium stearate, terra alba, talc, gelatin, agar, pectin, acacia, stearic acid, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils and are incorporated in a soft gelatin capsule shell.

Typical parenteral compositions consist of a solution or suspension of the compound or salt in a sterile aqueous or non-aqueous carrier optionally containing a parenterally acceptable oil, for example polyethylene glycol, polyvinylpyrrolidone, lecithin, arachis oil, or sesame oil.

Typical compositions for inhalation are in the form of a solution, suspension or emulsion that may be administered as a dry powder or in the form of an aerosol using a conventional propellant such as dichlorodifluoromethane or trichlorofluoromethane.

A typical suppository formulation comprises a compound of Formula (1) or a pharmaceutically acceptable salt thereof which is active when administered in this way, with a binding and/or lubricating agent, for example polymeric glycols, gelatins, cocoa-butter or other low melting vegetable waxes or fats or their synthetic analogues.

Typical transdermal formulations comprise a conventional aqueous or non-aqueous vehicle, for example a cream, ointment, lotion or paste or are in the form of a medicated plaster, patch or membrane.

Preferably the composition is in unit dosage form, for example a tablet, capsule or metered aerosol dose, so that the patient may administer to themselves a single dose.

Each dosage unit for oral administration contains suitably from 0.1 mg to 500 mg/Kg, and preferably from 1 mg to 100 mg/Kg, and each dosage unit for parenteral administration contains suitably from 0.1 mg to 100 mg, of a compound of Formula (I) or a pharmaceutically acceptable salt thereof calculated as the free acid. Each dosage unit for intranasal administration contains suitably 1–400 mg and preferably 10 to 200 mg per person. A topical formulation contains suitably 0.01 to 1.0% of a compound of Formula (I).

The daily dosage regimen for oral administration is suitably about 0.01 mg/Kg to 40 mg/Kg, of a compound of Formula (I) or a pharmaceutically acceptable salt thereof calculated as the free acid. The daily dosage regimen for parenteral administration is suitably about 0.001 mg/Kg to 40 mg/Kg, of a compound of the Formula (I) or a pharmaceutically acceptable salt thereof calculated as the free acid. The daily dosage regimen for intranasal administration and oral inhalation is suitably about 10 to about 500 mg/person. The active ingredient may be administered from 1 to 6 times a day, sufficient to exhibit the desired activity.

exhibit the desired activity.

These sulphonamide analogs may be used for the treatment of congestive heart failure, stroke, ischemic heart disease (angina, myocardial ischemia), cardiac arrhythmia, hypertension (essential and pulmonary), renal disease (acute and chronic renal failure/end stage renal disease) along with peripheral vascular disease (male erectile dysfunction, diabetic retinopathy, intermittent claudication/ischemic limb disease) and ischemic/hemorrhagic stroke, COPD, restenosis, asthma, neurogenic inflammation, migraine, metabolic vasculopathies, bone/cartilage/joint diseases, arthritis and other inflammatory diseases, fibrosis (e.g. pulmonary fibrosis), sepsis, atherosclerosis, dyslipidemia, addiction, schizophrenia, cognitive disorders/Alzheimers disease, impulsivity, anxiety, stress, depression, pain, neuromuscular function, diabetes, gastric reflux, gastric motility disorders, ulcers and genitourinary diseases.

The urotensin antagonist may be administered alone or in conjunction with one or more other therapeutic agents, said agents being selected from the group consisting of endothelin receptor antagonists, angiotensin converting enzyme (ACE) inhibitors, vasopeptidase inhibitors, diuretics, digoxin, and dual non-selective β-adrenoceptor and $\alpha_1$-adrenoceptor antagonists.

No unacceptable toxicological effects are expected when compounds of the invention are administered in accordance with the present invention.

The biological activity of the compounds of Formula (I) are demonstrated by the following tests:

Radioligand Binding:

HEK-293 cell membranes containing stable cloned human and rat GPR-14 (20 ug/assay) were incubated with 200 pM [125I] h-U-II (200 Ci/mmol$^{-1}$ in the presence of increasing concentrations of test compounds in DMSO (0.1 nM to 10 uM), in a final incubation volume of 200 ul (20 mM Tris-HCl, 5 mM MgCl2). Incubation was done for 30 minutes at room temperature followed by filtration GF/B filters with Brandel cell harvester. $^{125}$I labeled U-II binding was quantitated by gamma counting. Nonspecific binding was defined by $^{125}$I U-II binding in the presence of 100 nM of unlabeled human U-II. Analysis of the data was performed by nonlinear least square fitting.

$Ca^{2+}$-Mobilization:

A microtitre plate based $Ca^{2+}$-mobilization FLIPR assay (Molecular Devices, Sunnyvale, Calif.) was used for the functional identification of the ligand activating HEK-293 cells expressing (stable) recombinant GPR-14. The day following transfection, cells were plated in a poly-D-lysine coated 96 well black/clear plates. After 18–24 hours the media was aspirated and Fluo 3AM-loaded cells were exposed to various concentrations (10 nM to 30 uM) of test compounds followed by h-U-II. After initiation of the assay, fluorescence was read every second for one minute and then every 3 seconds for the following one minute. The inhibitory concentration at 50% (IC50)was calculated for various test compounds.

Inositol Phosphates Assays:

HEK-293-GPR14 cells in T150 flask were prelabeled overnight with 1 uCi myo-[$^3$H] inositol per ml of inositol free Dulbecco's modified Eagel's medium. After labeling, the cells were washed twice with Dulbecco's phosphate-buffered saline (DPBS) and then incubated in DPBS containing 10 mM LiCl for 10 min at 37° C. The experiment was initiated by the addition of increasing concentrations of h-U-II (1 pM to 1 μM) in the absence and presence of three different concentrations (0.3, 1 and 10 uM) of test compounds and the incubation continued for an additional 5 min at 37° C. after which the reaction was terminated by the addition of 10% (final concentration) trichloroacetic acid and centrifugation. The supernatants were neutralized with 100 ul of 1M Trizma base and the inositol phosphates were separated on AG 1-X8 columns (0.8 ml packed, 100–200 mesh) in formate phase. Inositol monophosphate was eluted with 8 ml of 200 mM ammonium formate. Combined inositol di and tris phosphate was eluted with 4 ml of 1M ammonium formate/0.1 M formic acid. Eluted fractions were counted in beta scintillation counter. Based on shift from the control curve $K_B$ was calculated.

Activity for the compounds of this invention range from (radioligand binding assay): Ki=1 nM–10000 nM (example 14, Ki=590 nM)

The following Examples are illustrative but not limiting embodiments of the present invention.

EXAMPLE 1

((R)-N-[-4-Chloro-3-(1-methyl-3-pyrrolidinyloxy)-phenyl]-4-bromo-2,5-dichlorothiophene-3-sulfonamide

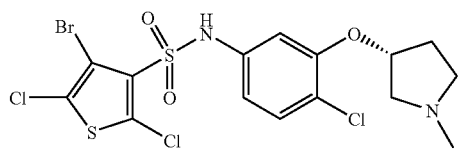

a) 2-Chloro-5-nitrophenol

2-Chloro-5-nitroanisole (310 g, 1.7 mol) was taken up in a mixture of 48% HBr (1.5 L) and AcOH (1.2 L) and heated at reflux for 3 days. The dark solution was allowed to cool to room temperature, poured into ice water (10 L), and let stand for 3 h. The resultant dull yellow solid was filtered, washed with water, and dried in vacuo (230 g, 79%): mp 115–117° C.

b) 2-Chloro-5-aminophenol

A solution of 2-chloro-5-nitrophenol (114 g, 0.66 mol) in ethyl acetate (500 mL) was treated with 5% Pt/C (510 mg, 0.5 weight %) and the mixture shaken under a hydrogen atmosphere (30 psi) for 6 h. The mixture was filtered through Celite® and the residue washed well with ethyl acetate. Evaporation of the ethyl acetate gave a solid (95 g, 100% crude yield) which was taken directly into the next step.

c) 4-Chloro-3-hydroxyphenylcarbamic acid tert-butyl ester

To a solution of 2-chloro-5-aminophenol (95 g, 0.66 mol) in THF (600 mL) was added a solution of di-tert-butyl dicarbonate (144 g, 0.66 mol) in THF (600 mL). The reaction was heated at reflux for 6 h, at which time it was allowed to cool to room temperature. The solvent was removed in vacuo and the residue diluted with ether (1000 mL) and washed with 1 M citric acid (2×1000 mL). The aqueous washings were extracted with ether (500 mL) and the combined organics washed with brine (500 mL), dried (MgSO$_4$), and concentrated. The resultant brown solid was triturated with hexanes and dried in vacuo to give 125 g (78%) of the title compound: mp 103–106° C.

d) 4-Chloro-3-((R)-1-methyl-pyrrolidin-3-yloxy) aniline

To a cooled (0° C.) solution of 4-chloro-3-hydroxyphenylcarbamic acid tert-butyl ester (55 g, 0.23 mol), (S)-1-methyl-pyrrolidin-3-ol (24 g, 0.24 mol), and triphenylphosphine (89 g, 0.34 mol) in THF (1.1 L) was added dropwise via addition funnel a solution of DIAD (67 mL, 0.34 mol) in THF (100 mL) over 1 h. The resultant solution was allowed to slowly warm to ambient temperature and maintained for 16 h. The THF was removed in vacuo and the residue treated with 6 N HCl (650 mL). The resultant mixture was stirred at room temperature for 4 h, at which time it was diluted with water (500 mL) and the filtered to remove the triphenylphosphine oxide. The filtrate was washed with EtOAc (3×1 L) and chloroform (5×1 L) to remove additional reaction byproducts. The aqueous layer was then basified with solid NaOH pellets and extracted with ether (2×1 L) and EtOAc (2×1 L). The combined organic layers were washed with saturated NaHCO$_3$ (2×1 L) and brine (1 L), dried (MgSO$_4$), and concentrated to give 40 g (80%) of the title compound: MS (ES+) m/e [M+H]$^+$ 227.

e) (R)-N-[4-Chloro-3-(1-methyl-3-pyrrolidinyloxy)-phenyl]-4-bromo-2,5-dichlorothiophene-3-sulfonamide To a solution of 4-chloro-3-((R)-1-methyl-pyrrolidin-3-yloxy) aniline (103 mg, 0.455 mmol) in 1,2-dichloromethane (2 mL) was added 4-bromo-2,5-dichloro-3-sulfonyl chloride (150 mg, 0.455 mmol). The resultant solution was maintained at ambient temperature for 18 h on a shaker, at which time the solution was evaporated and the solids dissolved in 0.5 mL of DMSO. The product in DMSO was purified by reverse phase HPLC to obtain 85 mg (36%) of the title compound: (ES+) m/e [M+H]$^+$ 521.

EXAMPLE 7a 2.4.5-Trichloro-thiophene-3-sulfonyl chloride

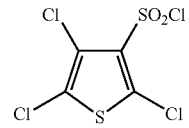

A mixture of 2,5-dichlorothiophene-3-sulfonyl chloride (1.2 g, 5 mmol) and sulfur monochloride (10 mg) in sulfuryl chloride (500 mg) was heated at 60° C. for 30 min, at which time was added dropwise a mixture of aluminum trichloride (10 mg) in sulfuryl chloride (500 mg). The reaction was heated at 60° C. for an additional 3 hours, at which time it was allowed to cool to ambient temperature. Cold water (20 mL) was added and the reaction extracted with dichloromethane (2×20 mL). The combined organic layers were washed with saturated sodium bicarbonate solution, dried (Mg$_2$SO$_4$) and concentrated to furnish a tan solid (420 mg, 33%).

EXAMPLE 8a 2,5-Dichloro-4-methylthiophene-3-sulfonyl chloride

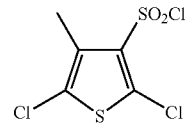

To a cooled (10° C.) solution of 3-methylthiophene (5 g, 50 mmol) in dichloromethane (15 mL) was added a solution of sulfuryl chloride (8.6 mL) in dichloromethane (5 mL). The reaction mixture was maintained at 10° C. for 30 minutes, then at ambient temperature for 16 hours. The reaction was concentrated and redissolved in dichloromethane (30 mL) and cooled to −10° C. To the cooled solution was added chlorosulfonic acid (2 mL, 100 mmol). The reaction was maintained at −10° C. for 30 minutes, then at ambient temperature for 16 hours, at which time it was poured into ice water (50 mL) and extracted with dichloromethane (50 mL). The organic layer was dried (Mg$_2$SO$_4$) and concentrated to furnish a brown oil (3.3 g, 25%).

Examples 2–8 were made as set forth in Example 1 by substituting the appropriate starting materials.

| Example | Compound | MS (ES+) m/e [M+H]⁺ |
|---|---|---|
| 2 | 5-Bromo-6-chloro-pyridin-3-sulfonic acid [4-chloro-3-((R)-1-methyl-pyrrolidin-3-yloxy)-phenyl]-amide (Chiral) | 481 |
| 3 | (S)-N-[4-Chloro-3-(1-methyl-3-pyrrolidinyloxy)-phenyl]-4,5-dibromothiophene-2-sulfonamide | 531 |
| 4 | (R)-N-[4-Chloro-3-(1-methyl-3-pyrrolidinyloxy)-phenyl]-4,5-dibromothiophene-2-sulfonamide | 531 |
| 5 | (R)-N-[4-Chloro-3-(1-methyl-3-pyrrolidinyloxy)-phenyl]-4-bromo-5-chlorothiophene-2-sulfonamide | 486 |
| 6 | (R)-N-[4-Chloro-3-(1-methyl-3-pyrrolidinyloxy)-phenyl]-(2,5-dimethyl-4-ethoxycarbonyl)-furan-3-sulfonamide | 457 |
| 7 | (R)-N-[4-chloro-3-(1-methyl-3-pyrrolidinyloxy)-phenyl]-2,4,5-trichloro-thiophene-3-sulfonamide (Chiral) | 475 |

-continued

| Example | Compound | MS (ES+) m/e [M+H]+ |
|---|---|---|
| 8 | Chiral (R)-N-[4-Chloro-3-(1-methyl-3-pyrrolidinyloxy)-phenyl]-2,5-dichloro-4-methyl-thiophene-3-sulfonamide | 455 |

EXAMPLES 9–11

Substituting 5-amino-o-cresol for 2-chloro-5-aminophenol and substituting various sulfonyl chlorides for 2,4,5-trimethoxybenzenesulfonyl chloride, examples 9–11 were prepared following the procedures described in 1c-1e:

| Example | Compound | MS (ES+) m/e [M+H]+ |
|---|---|---|
| 9 | Chiral 4-Bromo-2,5-dichloro-thiophene-3-sulfonic acid [4-methyl-3-((R)-1-methyl-pyrrolidin-3-yloxy)-phenyl]-amide | 500 |
| 10 | Chiral 5-Bromo-6-chloro-pyridin-3-sulfonic acid [4-methyl-3-((R)-1-methyl-pyrrolidin-3-yloxy)-phenyl]-amide | 461 |
| 11 | Chiral 4-Bromo-2,5-dichloro-thiophene-3-sulfonic acid [4-methyl-3-((S)-1-methyl-pyrrolidin-3-yloxy)-phenyl]-amide | 500 |

EXAMPLE 12

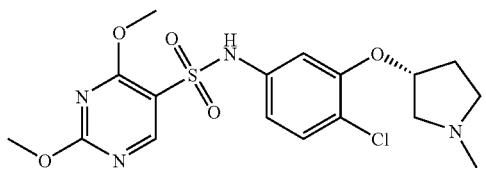

2,4-Dimethoxy-pyrimidine-5-sulfonic acid [4-chloro-3-((R)-1-methyl-pyrrolidin-3-yloxy)-phenyl]-amide a) 2,4-Dihydroxy-pyrimidine-5-sulfonic acid [4-chloro-3-((R)-1-methyl-pyrrolidin-3-yloxy)-phenyl]-amide (R)-3-(1-Methyl-3-pyrrolidinyl)-4-chloroaniline (500 mg, 2 mmol) was dissolved in pyridine (1 mL). 2,4-Dihydroxy-pyrimidine-5-sulfonyl chloride (840 mg, 4 mmol) was added and the mixture was allowed to stir at room temperature for 16 hours. The mixture was concentrated and the residue purified by reverse phase HPLC (500 mg, 63%): MS (ES+) m/e [M+H]+ 401.

b) A solution of 2,4-dihydroxy-pyrimidine-5-sulfonic acid [4-chloro-3-((R)-1-methyl-pyrrolidin-3-yloxy)-phenyl]-amide (1.5 g, 3.8 mmol) in phosphorus(III)oxychloride (300 mL) was heated at reflux for 5 hours, at which time the reaction mixture was concentrated. A portion of the residue (200 mg, 0.5 mmol) was stirred in methanol (25 mL) for 16 hours, at which time the reaction was concentrated. Purification of the residue by reverse phase HPLC furnished the title compound (6.3 mg, 1.4%): MS (ES+) m/e [M+H]+ 429.

Examples 13 and 14 were made as set forth in Example 12 by substituting the appropriate starting materials.

EXAMPLE 15

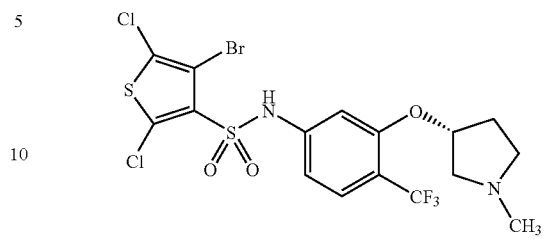

4-Bromo-2,5-dichloro-thiophene-3-sulfonic acid [((R)-1-methyl-pyrrolidin-3-yloxy)-4-trifluoromethyl-phenyl]-amide hydrochloride a) 2-Fluoro-4-nitrobenzotrifluoride A solution of 4-amino-2-fluorobenzotrifluoride (25.0 g, 0.14 mol, 1.0 eq) in trifluoroacetic acid (140 ml) was heated to reflux then was treated with the dropwise addition of 50% hydrogen peroxide (66.7 ml, 1.18 mol, 8.4 eq) over 35 min. The reaction was heated at reflux for 1.5 hrs further then cooled to ambient temperature. Poured into ice-water (1 L) then stirred overnight. The oil that separated was collected (decanting the water phase) then diluted with diethyl ether (150 ml). The ether solution was washed with aqueous 10% HCl (100 ml), saturated aqueous sodium bicarbonate (2×100 ml), and brine (100 ml) then dried over anhydrous magnesium sulphate. Evaporation under reduced pressure gave an orange-brown oil. Distillation (14 torr, 88–90° C.) gave the product as a yellow liquid (15.0 g, 51%)

| Example | | Compound | MS (ES+) m/e [M+H]+ |
|---|---|---|---|
| ![structure 13] 13 | Chiral | 2,4-Diethoxy-pyrimidine-5-sulfonic acid [4-chloro-3-((R)-1-methyl-pyrrolidin-3-yloxy)-phenyl]-amide | 457 |
| ![structure 14] 14 | Chiral | 2-Chloro-4-(2,2,2-trifluoro-ethoxy)-pyrimidine-5-sulfonic acid [4-chloro-3-((R)-1-methyl-pyrrolidin-3-yloxy)-phenyl]-amide | 501 | b) 2-((R)-1-Methyl-pyrrolidin-3-yloxy)-4-nitrobenzotrifluoride

A solution of 2-fluoro-4-nitrobenzotrifluoride (12.4 g, 59.3 mmol, 1.0 eq) and (R)-1-methyl-pyrrolidin-3-ol (6.0 g, 59.3 mmol, 1.0 eq) in anhydrous tetrahydrofuran (150 ml) was cooled to 0° C. then slowly treated with portions of 60% sodium hydride (4.7 g, 0.12 mol, 2 eq) over 5 min. Without removing the ice bath, the reaction was allowed to come to room temperature and stir for 48 hrs. Quenched with water (50 ml) and brine (100 ml) then extracted into diethyl ether (5×100 ml). Extracts dried over anhydrous magnesium sulfate and decolorizing charcoal for 1 hr. Filtered through Celite. The filtrate was treated with silica (35 g) then evaporated to give the crude product suspended on silica. Column chromatography on silica (1% MeOH/EtOAc→5% MeOH/EtOAc) gave the product (Rf≡0.3 in 1% MeOH/EtOAc) as an orange oil (7.85 g, 46%).

c) 3-((R)-1-Methyl-pyrrolidin-3-yloxy)-4-trifluoromethyl-phenylamine

A solution of 2-((R)-1-Methyl-pyrrolidin-3-yloxy)-4-nitrobenzotrifluoride (7.8 g, 26.9 mmol) in ethyl acetate (50 ml) was treated with 10% platinum on carbon (200 mg) then subjected to 40 psi hydrogen pressure for 3 hrs. The slurry was treated with anhydrous magnesium sulfate (5 g) then filtered through a pad of Celite. The filter cake was rinsed with ethyl acetate (2×25 ml) then the filtrate was evaporated under reduced pressure to an oil. This oil was evaporated twice for dichloromethane (50 ml) to remove trapped ethyl acetate. This gave the product as a clear light brown oil that solidified on standing (6.9 g, 99%): LCMS 249 ($M^+$+H).

d) 4-Bromo-2,5-dichloro-thiophene-3-sulfonic acid [((R)-1-methyl-pyrrolidin-3-yloxy)-4-trifluoromethyl-phenyl]-amide hydrochloride To a solution of ((R)-1-Methylpyrrolidin-3-yloxy)-trifluoromethyl-phenylamine (250 mg, 0.96 mmol) in anhydrous chloroform (5 ml) was added 4-bromo-2,5-dichlorothiophene-3-sulfonyl chloride (317 mg, 0.96 mmol), neat. After stirring at ambient temperature for 3 days, the solvent was removed under reduced pressure. The resulting oilly residue was taken into methylene choride and washed with 1% sodium hydroxide solution and brine then dried over anhydrous magnesium sulfate. The filtered solution was evaporated to an oil that was purified by flash chromatography on silica (1% methanol/Ethyl acetate gradient to 5% methanol/Ethyl acetate) to give the free base as a colorless oil. This was taken into methylene chloride (1 ml) and treated with 1N hydrogen chloride in diethyl ether (1 ml). Evaporation under preduced pressure afforded 125 mg (22%) of the title compound as a pale yelow solid: MS (ES+) m/e [M+H]$^+$ 553.

EXAMPLES 16–20

Substituting 3-((R)-1-methyl-pyrrolidin-3-yloxy)-4-trifluoromethyl-phenylamine for (R)-3-(1-methyl-3-pyrrolidinyl)-4-chloroaniline and substituting various sulfonyl chlorides for 2,4,5-trimethoxybenzenesulfonyl chloride, examples 16–20 were prepared following the procedure described in 1e:

| Example | | Compound | MS (ES+) m/e [M+H]$^+$ |
|---|---|---|---|
| 16 | Chiral | 4-Bromo-5-chloro-thiophene-2-sulfonic acid [3-((R)-1-methyl-pyrrolidin-3-yloxy)-4-trifluoromethyl-phenyl]-amide | 519 |
| 17 | Chiral | 4,5-Dibromo-thiophene-2-sulfonic acid [3-((R)-1-methylpyrrolidin-3-yloxy)-4-trifluoromethyl-phenyl]-amide | 565 |

-continued

| Example | Compound | MS (ES+) m/e [M+H]+ |
|---|---|---|
| 18 | Chiral 2,5-Dichloro-thiophene-3-sulfonic acid [3-((R)-1-methyl-pyrrolidin-3-yloxy)-4-trifluoromethyl-phenyl]-amide | 475 |
| 19 | Chiral 5-Bromo-6-chloro-pyridine-3-sulfonic acid [3-((R)-1-methyl-pyrrolidin-3-yloxy)-4-trifluoromethyl-phenyl]-amide | 515 |
| 20 | Chiral 2,4,5-Trichloro-thiophene-3-sulfonic acid [3-((R)-1-methyl-pyrrolidin-3-yloxy)-4-trifluoromethyl-phenyl]-amide | 509 |

EXAMPLE 21

Formulations for pharmaceutical use incorporating compounds of the present invention can be prepared in various forms and with numerous excipients. Examples of such formulations are given below.

| Tablets/Ingredients | Per Tablet |
|---|---|
| 1. Active ingredient (Cpd of Form. I) | 40 mg |
| 2. Corn Starch | 20 mg |
| 3. Alginic acid | 20 mg |
| 4. Sodium Alginate | 20 mg |
| 5. Mg stearate | 1.3 mg |
|  | 2.3 mg |

Procedure for Tablets:

Step 1: Blend ingredients No. 1, No. 2, No. 3 and No. 4 in a suitable mixer/blender.

Step 2: Add sufficient water portion-wise to the blend from Step 1 with careful mixing after each addition. Such additions of water and mixing until the mass is of a consistency to permit its conversion to wet granules.

Step 3: The wet mass is converted to granules by passing it through an oscillating granulator using a No. 8 mesh (2.38 mm) screen.

Step 4: The wet granules are then dried in an oven at 140° F. (60° C.) until dry.

Step 5: The dry granules are lubricated with ingredient No. 5.

Step 6: The lubricated granules are compressed on a suitable tablet press.

Inhalant Formulation

A compound of Formula I, (1 mg to 100 mg) is aerosolized from a metered dose inhaler to deliver the desired amount of drug per use.

Parenteral Formulation

A pharmaceutical composition for parenteral administration is prepared by dissolving an appropriate amount of a compound of formula I in polyethylene glycol with heating. This solution is then diluted with water for injections Ph Eur. (to 100 ml). The solution is then sterilized by filtration through a 0.22 micron membrane filter and sealed in sterile containers.

The above specification and Examples fully disclose how to make and use the compounds of the present invention. However, the present invention is not limited to the particular embodiments described hereinabove, but includes all modifications thereof within the scope of the following claims. The various references to journals, patents and other publications which are cited herein comprise the state of the art and are incorporated herein by reference as though fully set forth.

What is claimed is:

1. A compound of Formula (I):

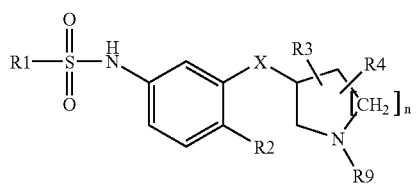

Formula (I)

wherein:
R1 is phenyl, thienyl, furanyl, pyrroyl, pyridinyl, oxazoyl, indoyl, triazinyl, imidazoyl, pyrimidinyl, oxadiazoyl, pyrazoyl, triazoyl, thiazoyl, thiadiazoyl, or pyrazinyl substituted or unsubstituted by one, two, three, four or five of any of the following: halogen, $CF_3$, $OCF_3$, $SCF_3$, $NO_2$, CN, $C_{1-6}$ alkyl, $C_{1-6}$ alkoxy, $NR_5R_6$, $CONR_7R_8$, $SC_{1-6}$ alkyl, $CO_2(C_{1-6}$ alkyl), or $C_{1-6}$ alkyl-$CO_2(C_{1-6}$ alkyl);
$R_2$ is hydrogen, halogen, $CF_3$, CN, or $C_{1-4}$ alkyl;
$R_3$, $R_4$, $R_7$, and $R_8$ are independently hydrogen, $C_{1-6}$ alkyl, or benzyl;
$R_5$, $R_6$, and $R_9$, are independently hydrogen or $C_{1-6}$ alkyl;
X is O, S, or $CH_2$;
n is 0, 1 or 2;
or a pharmaceutically acceptable salt thereof;
provided when n is 1, $R_1$ is not phenyl.

2. A compound according to claim 1 wherein R1 is thienyl, or furanyl substituted or unsubstituted by one, two, three, four, or five of any of the following: halogen, $CF_3$, $OCF_3$, CN, $C_{1-6}$ alkyl, $C_{1-6}$ alkoxy, $CO_2(C_{1-6}$ alkyl), $C_{1-6}$ alkyl-$CO_2(C_{1-6}$ alkyl), or $NO_2$; $R_2$ is hydrogen, halogen, $CF_3$, or $C_{1-4}$ alkyl; $R_3$ is hydrogen; $R_4$ is hydrogen; $R_9$ is hydrogen or $C_{1-6}$ alkyl; X is O; and n is 1.

3. A compound according to claim 1 wherein $R_1$ is thienyl substituted or unsubstituted by one, two, three, or four of the following: halogen, $CF_3$, CN, methyl, methoxy; $R_2$ is halogen or $CF_3$, $R_3$ is hydrogen; $R_4$ is hydrogen; $R_9$ is hydrogen or $C_{1-6}$ alkyl; X is O; and n is 1.

4. A compound according to claim 1 chosen from the group consisting of:
(S)-N-[4-Chloro-3-(1-methyl-3-pyrrolidinyloxy)-phenyl] 4,5-dibromothiophene-2-sulfonamide;
(R)-N-[4-Chloro-3-(1-methyl-3-pyrrolidinyloxy)-phenyl] 4,5-dibromothiophene-2-sulfonamide;
(R)-N-[4-Chloro-3-(1-methyl-3-pyrrolidinyloxy)-phenyl] 4-bromo-5-chlorothiophene-2-sulfonamide;
(R)-N-[4-Chloro-3-(1-methyl-3-pyrrolidinyloxy)-phenyl] 4-bromo-2,5-dichlorothiophene-3-sulfonamide;
(R)-N-[4-Chloro-3-(1-methyl-3-pyrrolidinyloxy)-phenyl]-2,4,5-trichloro-thiophene-3-sulfonamide;
(R)-N-[4-Chloro-3-(1-methyl-3-pyrrolidinyloxy)-phenyl]-2,5-dichloro-4-methyl-thiophene-3-sulfonamide;
4-Bromo-2,5-dichloro-thiophene-3-sulfonic acid [4-methyl-3-((R)-1-methyl-pyrrolidin-3-yloxy)-phenyl]-amide;
4-Bromo-2,5-dichloro-thiophene-3-sulfonic acid [4-methyl-3-((S)-1-methyl-pyrrolidin-3-yloxy)-phenyl]-amide;
4-Bromo-2,5-dichloro-thiophene-3-sulfonic acid [3-(1-methyl-pyrrolidin-3-yloxy)-4-trifluoromethyl-phenyl]-amide;
4-Bromo-5-chloro-thiophene-2-sulfonic acid [3-((R)-1-methyl-pyrrolidin-3-yloxy)-4-trifluoromethyl-phenyl]-amide;
4,5-Dibromo-thiophene-2-sulfonic acid [3-((R)-1-methyl-pyrrolidin-3-yloxy)-4-trifluoromethyl-phenyl]-amide;
2,5-Dichloro-thiophene-3-sulfonic acid [3-((R)-1-methyl-pyrrolidin-3-yloxy)-4-trifluoromethyl-phenyl]-amide;
5-Bromo-6-chloro-pyridine-3-sulfonic acid [3-((R)-1-methyl-pyrrolidin-3-yloxy)-4-trifluoromethyl-phenyl]-amide;
2,4,5-Trichloro-thiophene-3-sulfonic acid [3-((R)-1-methyl-pyrrolidin-3-yloxy)-4-trifluoromethyl-phenyl]-amide;
(R)-N-[4-Chloro-3-(1-methyl-3-pyrrolidinyloxy)-phenyl]-(2,5-dimethyl-4-ethoxycarbonyl)-furan-3-sulfonamide;
2,4-Dimethoxy-pyrimidine-5-sulfonic acid [4-chloro-3-((R)-1-methyl-pyrrolidin-3-yloxy)-phenyl]-amide;
2,4-Diethoxy-pyrimidine-5-sulfonic acid [4-chloro-3-((R)-1-methyl-pyrrolidin-3-yloxy)-phenyl]-amide;
2-Chloro-4-(2,2,2-trifluoro-ethoxy)-pyrimidine-5-sulfonic acid [4-chloro-3-((R)-1-methyl-pyrrolidin-3-yloxy)-phenyl]-amide;
5-Bromo-6-chloro-pyridine-3-sulfonic acid [4-chloro-3-((R)-1-methyl-pyrrolidin-3-yloxy)-phenyl]-amide; or
5-Bromo-6-chloro-pyridine-3-sulfonic acid [4-methyl-3-((R)-1-methyl-pyrrolidin-3-yloxy)-phenyl]-amide.

5. A compound according to claim 1 chosen from the group consisting of:
(R)-N-[4-Chloro-3-(1-methyl-3-pyrrolidinyloxy)-phenyl]-4-bromo-2,5-dichlorothiophene-3-sulfonamide;
4-Bromo-2,5-dichloro-thiophene-3-sulfonic acid N-[3-(1-methyl-pyrrolidin-3-yloxy)-4-trifluoromethyl-phenyl]-amide; or
2,4,5-Trichloro-thiophene-3-sulfonic acid [3-((R)-1-methyl-pyrrolidin-3-yloxy)-4-trifluoromethyl-phenyl]-amide.

6. A pharmaceutical composition comprising a compound of formula (I) of claim 1 and a pharmaceutically acceptable carrier or excipient.

* * * * *